(12) United States Patent
Babaeizadeh et al.

(10) Patent No.: US 9,730,633 B2
(45) Date of Patent: Aug. 15, 2017

(54) REAL-TIME AIRWAY CHECK STATUS INDICATOR

(75) Inventors: Saeed Babaeizadeh, Brookline, MA (US); Eric Helfenbein, Sunnyvale, CA (US); Sophia Huai Zhou, Camarillo, CA (US)

(73) Assignee: Koninklijke Philips N.V., Eindhoven (NL)

( * ) Notice: Subject to any disclaimer, the term of this patent is extended or adjusted under 35 U.S.C. 154(b) by 561 days.

(21) Appl. No.: 13/982,048

(22) PCT Filed: Feb. 21, 2012

(86) PCT No.: PCT/IB2012/050774
§ 371 (c)(1),
(2), (4) Date: Jul. 26, 2013

(87) PCT Pub. No.: WO2012/114262
PCT Pub. Date: Aug. 30, 2012

(65) Prior Publication Data
US 2013/0324872 A1 Dec. 5, 2013

Related U.S. Application Data

(60) Provisional application No. 61/576,872, filed on Dec. 16, 2011, provisional application No. 61/445,192, filed on Feb. 22, 2011.

(51) Int. Cl.
*A61B 5/00* (2006.01)
*A61B 5/083* (2006.01)
(Continued)

(52) U.S. Cl.
CPC ............ *A61B 5/4848* (2013.01); *A61B 5/082* (2013.01); *A61B 5/0836* (2013.01); *A61B 5/743* (2013.01);
(Continued)

(58) Field of Classification Search
CPC ........ A61B 5/082; A61B 5/0836; A61B 5/743
See application file for complete search history.

(56) References Cited

U.S. PATENT DOCUMENTS

| 4,728,499 A | 3/1988 | Fehder |
|---|---|---|
| 4,994,117 A | 2/1991 | Fehder |

(Continued)

FOREIGN PATENT DOCUMENTS

| CN | 87105619 A | 2/1988 |
|---|---|---|
| CN | 101014311 A | 8/2007 |

(Continued)

*Primary Examiner* — Jacqueline Cheng
*Assistant Examiner* — Angeline Premraj

(57) ABSTRACT

Immediately after airway placement and/or following any patient transfer, an automated program may be activated in a CO2 monitoring device to provide an airway device placement check. The automated program needs time to determine if the airway placement has been successful or not. During analysis of CO2 respiration data by the program, real-time feedback is displayed to the user as soon as the airway check program is activated until the time that a final decision on the success of airway placement is made. The real-time feedback displays one or more indicators of the progress of the program toward a determination of a successful or failed placement.

20 Claims, 7 Drawing Sheets

(51) Int. Cl.
*A61M 16/00* (2006.01)
*A61B 5/08* (2006.01)
*A61M 16/04* (2006.01)

(52) U.S. Cl.
CPC ........ *A61M 16/0051* (2013.01); *A61M 16/04* (2013.01); *A61M 2016/0413* (2013.01); *A61M 2230/06* (2013.01); *A61M 2230/205* (2013.01); *A61M 2230/30* (2013.01); *A61M 2230/432* (2013.01)

(56) References Cited

U.S. PATENT DOCUMENTS

| | | |
|---|---|---|
| 6,709,403 B1 | 3/2004 | Ratner |
| 8,147,419 B2 | 4/2012 | Krauss et al. |
| 9,039,629 B2 | 5/2015 | Zhou et al. |
| 2004/0236240 A1 | 11/2004 | Kraus et al. |
| 2006/0060202 A1 | 3/2006 | Flynn et al. |
| 2006/0087325 A1* | 4/2006 | Ariav ............... A61B 5/02444 324/637 |
| 2007/0261698 A1 | 11/2007 | Palatnik |
| 2008/0039735 A1* | 2/2008 | Hickerson ............ A61B 5/082 600/532 |
| 2010/0052608 A1 | 3/2010 | Ota et al. |
| 2010/0106208 A1 | 4/2010 | Freeman |
| 2011/0040713 A1 | 2/2011 | Colman et al. |
| 2013/0324872 A1 | 12/2013 | Babaeizadeh et al. |

FOREIGN PATENT DOCUMENTS

| | | |
|---|---|---|
| WO | 2010052608 A1 | 5/2010 |
| WO | 2015052608 A1 | 4/2015 |

\* cited by examiner

REAL-TIME AIRWAY CHECK STATUS INDICATOR

CROSS-REFERENCE TO PRIOR APPLICATIONS

This application is the U.S. National Phase application under 35 U.S.C. §371 of International Application No. PCT/IB2012/050774, filed on 2012 Feb. 21, which claims the benefit of U.S. Provisional Patent Application No. 61/576,872, filed on 2011 Dec. 16 and U.S. Provisional Patent Application No. 61/445,192, filed on 2011 Feb. 22. These applications are hereby incorporated by incorporated herein.

This invention relates to medical carbon dioxide ($CO_2$) monitoring systems and, in particular, to a $CO_2$ monitoring system that provides a real time indication of the success or failure of intubation of a patient.

$CO_2$ monitoring systems are usually found in hospital surgical suites and intensive care units to monitor a patient's respiration. Generally these systems are sophisticated and sizeable ventilation systems which monitor the oxygen intake and respiratory $CO_2$ of a patient. However, there are other scenarios where $CO_2$ monitoring is desirable. One is during intubation where air is being supplied to a patient by a hand-operated respiration device. Another is during the application of CPR to a patient stricken by cardiac arrest. A portable unit is desirable in such situations, such as the MRx defibrillator monitor produced by Philips Healthcare (Andover, Mass.), which may be used in a hospital but is portable and can be taken to the site of an accident or location of a stricken patient.

When a patient is intubated, the patient has often just suffered cardiac arrest or other serious affliction and may be breathing only shallow breaths or have gone a considerable period of time without breathing at all, either naturally or with assistance. With intubation of a respiration device assisted respiration can be provided immediately. It is important that the airway device be properly placed in the trachea and not improperly placed in the esophagus. Misplacement of airway devices inserted by emergency medical services personnel during out-of-hospital cardiac arrest can be a life-threatening problem. Although the manual use of colorimetric end-tidal carbon dioxide ($etCO_2$) detectors or real time capnography has reduced the incidence of misplaced airways, the validation process of successful intubation remains cumbersome and time-consuming.

In scenarios where $CO_2$ monitoring devices are being used, it is desirable to automatically provide an airway placement check that can be initiated immediately after airway placement and following any patient transfer. This can be accomplished by using a $CO_2$ analysis program integrated into the $CO_2$ monitoring device. The above-mentioned MRx defibrillator monitor contains such a $CO_2$ analysis program which can be used in a hospital or at the site of an accident or location of a patient stricken by cardiac arrest. The emergency medical person attending the patient can activate the $CO_2$ analysis program by pushing a button at anytime. After activation, the analysis program analyses the $CO_2$ waveform for a number of seconds before making a decision on the success of the airway placement. This delay is necessary because the $CO_2$ analysis program will need to see several valid breaths before it decides if the airway placement has been successful. Alternatively, the system will wait for a period of time without seeing valid breaths to determine that the airway placement has not been successful. This delay, which can be twenty seconds long, may seem even longer in a stressful emergency situation such as managing a patient who is not breathing and has been stricken by cardiac arrest out in the field.

Accordingly it is desirable to be able to quickly provide real time feedback to the user as soon as the airway check program is activated and during its progress until a final decision on the success of airway placement is made. This real-time feedback should indicate the status of the airway check in progress and should be distinctly and unambiguously visible to the rescuer.

In accordance with the principles of the present invention, an automated $CO_2$ monitoring system is described which provides real-time visual feedback as the status of placement of an airway device is analyzed. The visual feedback comprises one or more indicators of progress or status toward a placement status decision, including a graphical display of the breaths of the patient, a continuously updated progress indicator toward a determination of the success or failure of an intubation, time-delineated visual indicators of the determination of a true breath, and a colored or illuminated indicator of the instantaneous and final determination of the success or failure of airway device placement. This visual feedback is preferably displayed in vividly distinct colors on a color monitor such as that of the MRx monitor defibrillator.

Figure 1:
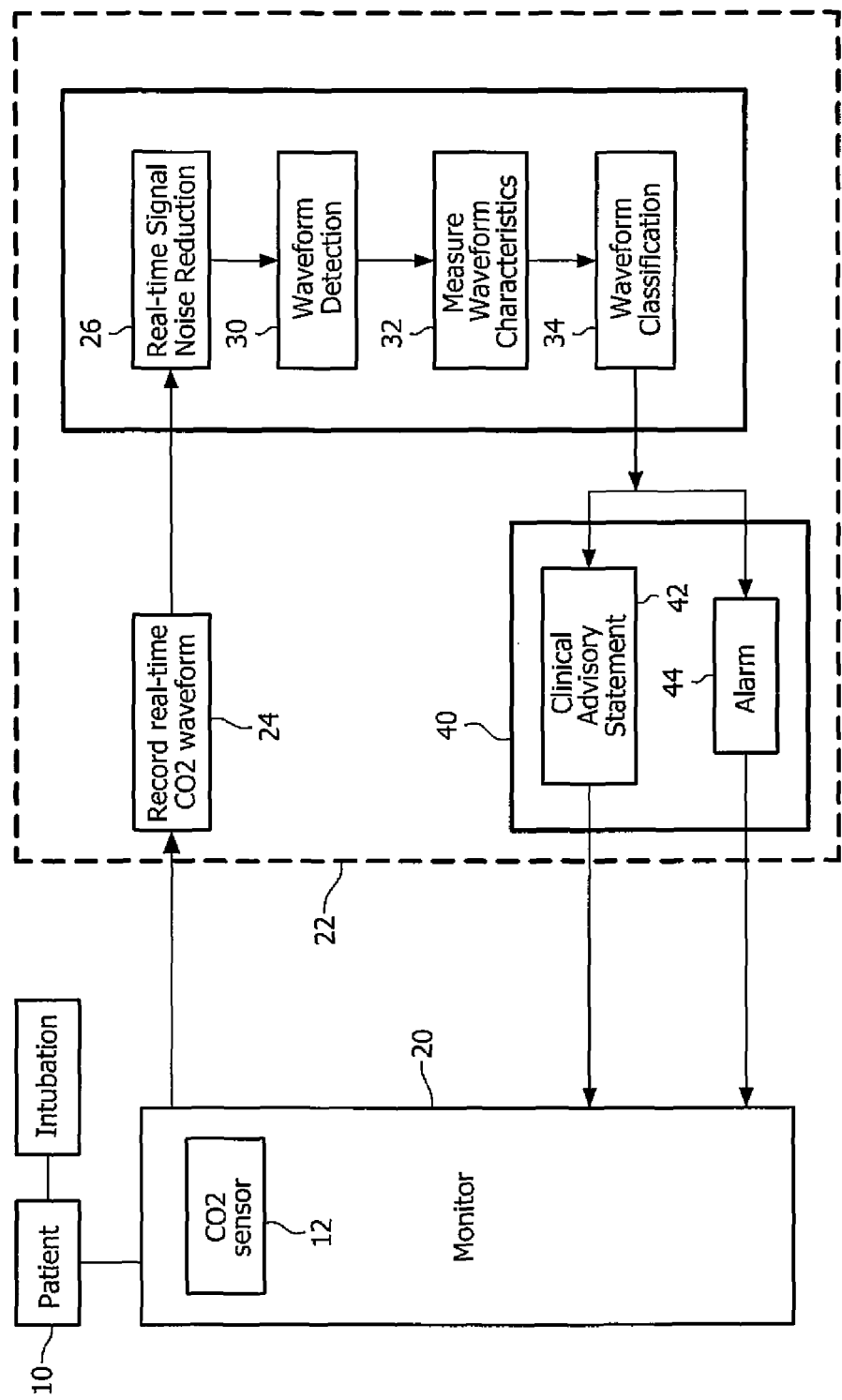
FIG. 1 illustrates in block diagram form a $CO_2$ monitoring system of the present invention being used with a patient undergoing intubation.

Referring first to FIG. 1, a $CO_2$ monitoring system 20 of the present invention is shown in block diagram form which is being used to monitor a patient 10 who is undergoing intubation. In a constructed embodiment the monitoring system 20 is integrated into the MRx monitor defibrillator. The respiratory gases of the patient are conducted to a $CO_2$ sensor 12 of the monitor, which senses the $CO_2$ content of the patient's expiration gases. The $CO_2$ measurement signals from the sensor 12 are digitized into digital samples which are recorded as shown at 24 of the processing section 22 of the monitor 20. The $CO_2$ signal samples are analyzed for noise content at 26 and may also undergo noise reduction. One technique for analyzing the noise content is to analyze the high frequency content of the signal samples. A clean $CO_2$ signal will exhibit relatively little high frequency content. The noise level of the signals may be reduced by processing them with a digital low pass filter at 26 of the monitoring section 22. Acceptable CO2 signals then undergo waveform detection at 30. One technique for detecting the CO2 waveform is to take the difference of successive samples, which effectively detects the slope of the waveform. A normal CO2 waveform will exhibit a steeply rising slope as the patient begins to exhale, a relatively flat top during exhalation, and a steeply falling slope as exhalation ends and the patient draws another breath, as discussed more fully below. Certain characteristics of the detected waveform are then measured at 32. These characteristics may include the baseline of the waveform, the height or amplitude of the waveform, the frequency of the waveform, the rhythm of the waveform, the corners of the waveform, the slopes of the waveform, and characteristics of the shape of the waveform. The measured characteristics are then classified at 34 to assess whether the waveform exhibits the characteristics of normal respiration for the treatment being applied, intubation, or are characteristic of a particular difficulty which may be encountered during a particular treatment regimen. The respiration data is coupled to a processor 40 for true breath and airway placement analysis. If a problem or difficulty is detected, an alarm 44 may be sounded or displayed to the clinician, or a clinical advisory statement 42 issued to advise the clinician that a particular problem or difficulty should be investigated. In the constructed embodiment the clinical advisory statement comprises the real-time airway status indicator described below, which is displayed on the color display of the monitor.

When the CO2 monitoring system is coupled to the patient, it should be set to identify the treatment being applied to the patient, such as intubation, CPR, or ventilation. This may be done by a manual switch or input to the monitoring system which set by the clinician. The setting may also be done automatically by the particular treatment device being used. For instance, when the air conduit of an intubation device is connected to the monitor 20, the monitor may sense the connection of the air conduit and thereby is informed that intubation is being monitored. The identification of the treatment regimen will condition the monitor 20 to be particularly sensitive to respiratory conditions which may be expected during the treatment regimen being applied.

Figure 2:
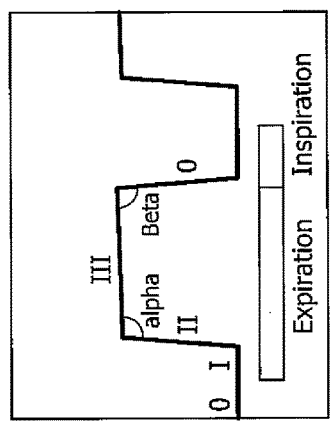
FIG. 2 illustrates standardized parameters of a $CO_2$ waveform.
Figure 3:
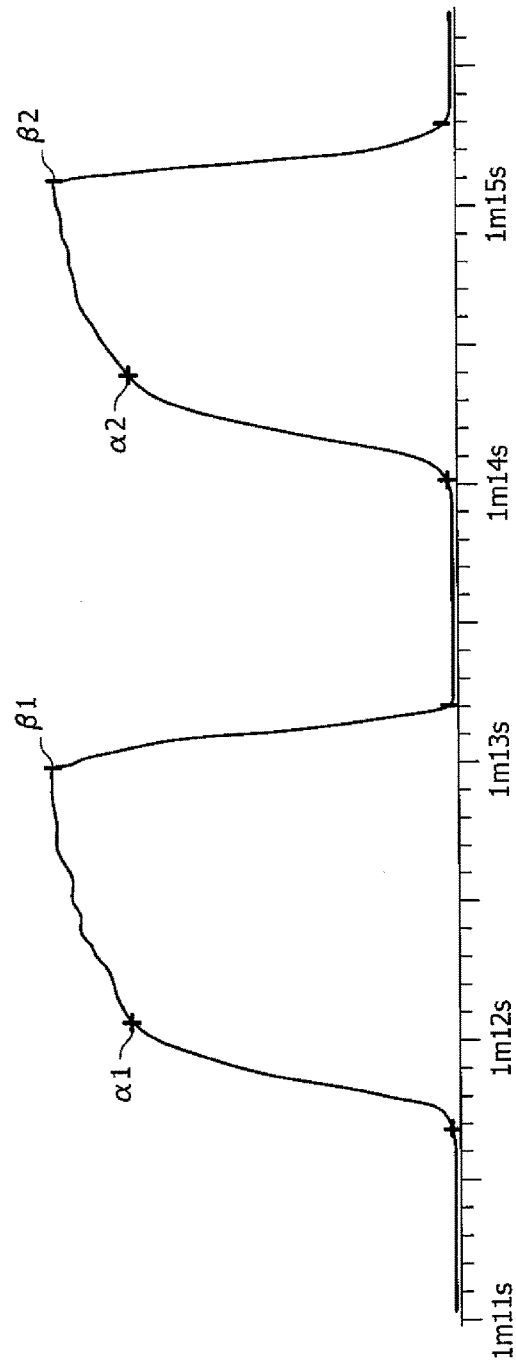
FIG. 3 illustrates a typical $CO_2$ waveform sequence.

FIG. 2 illustrates the standard parameters of a normal CO2 waveform. When the patient exhales and the expiration phase begins, the waveform will rise from a baseline I with a steep slope II until a sustained level III of CO2 content of the exhaled air is attained. The waveform will exhibit a corner alpha ($\alpha$) when the sustained level is reached. When the patient finishes exhaling the waveform will drop from a corner beta ($\beta$) at the start of the inspiration phase 0. The waveform will then repeat in this manner at the frequency and periodicity of the patient's respiration. An actual respiration waveform trace is shown in FIG. 3 along a horizontal time scale. The waveform is seen to have alpha points $\alpha$ 1 and $\alpha$ 2 at inflection points during the initial rise of the waveform, and sharply defined beta points $\beta$1 and $\beta$2 at the onset of inspiration and the fall of the waveform. Other characteristics such as the maximum amplitude, average height, waveform duration, and waveform frequency are also apparent in this illustration.

In accordance with the principles of the present invention, an automated program in the processor 40 analyzes the CO2 respiration waveform to check the status of the airway placement. The waveform comprises a flow of digitized CO2 samples fed into the program from the CO2 sensor 12. The program analyzes all samples within a time interval to make a decision on the success of the airway placement. To make such decision, the program may need to find valid (true) breaths in the CO2 waveform and check them against classification criteria to decide if the airway placement was successful. A constructed embodiment of the invention can access and use these interim steps in the analysis, internal to the automated program, to provide visual real-time feedback on which direction (toward airway success or failure) the analysis is progressing. For example, if the program is not finding a breath although CO2 samples are coming in, the final airway check decision is more likely to be failed than to be successful.

The following drawings illustrate the design and operation of an example of a real-time airway status display of the present invention. The constructed embodiment is displayed on a color display with colors that vividly indicate the progress of the airway placement analysis. Green is an indication that airway placement was successful or that the analysis is trending toward a determination of successful placement. Red is an indication that airway placement has failed. All other colors are indeterminate and may be tinted or shaded to indicate trending as illustrated below.

The constructed embodiment operates in accordance with the following protocol. The display shows a twenty second period of airway analysis, which is based on the assumption that complete determination of airway placement may take up to twenty seconds. Initially the color indicators are yellow, indicating an indeterminate state, and remain yellow for 5 seconds. Absent favorable information, the color trending is toward red. The color indicators are updated with the reception or analysis of each new CO2 sample. If no true breath is found in the first ten seconds of analysis, the color changes to red. A color indicator changes to or trends toward green if a true breath is validated, that is, meets predetermined criteria for a true breath. If an indicator turns green it will remain green for a pre-determined period of time, 2 seconds in the following examples, and will remain green for ever-increasing periods of time if successive true breaths are validated. Four types of visual indicators are shown in the following display examples: a continuously updated graphical display of the breaths of the patient, a continuously updated dynamic progress bar on the analyzed success or failure of an intubation, time-delineated indicator bars of the validation of a true breath, and a colored indicator of the instantaneous and final determination of the success or failure of an intubation. An implementation of the present invention should contain one or more such visual indicators.

Figure 4:
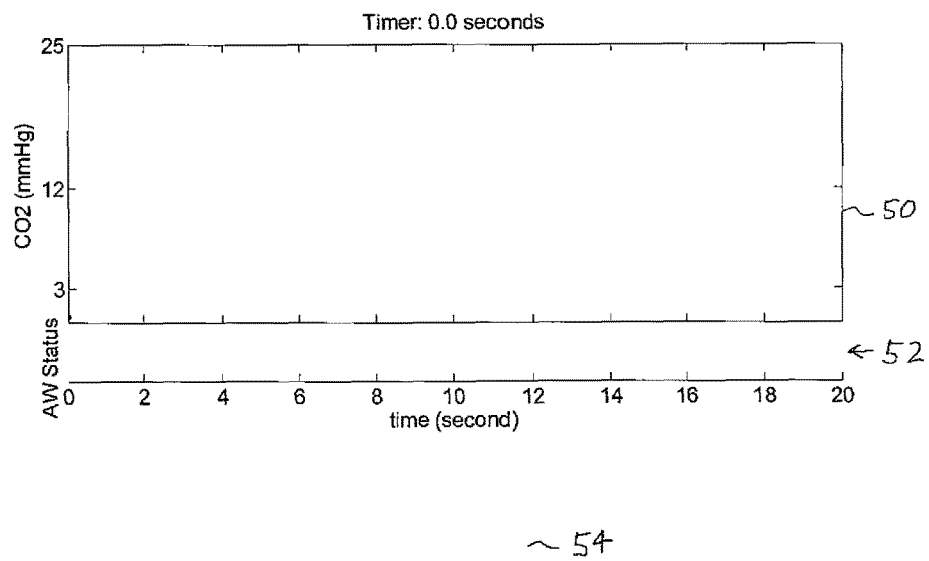
FIG. 4 illustrates a real-time airway status indicator display of the present invention when initialized.

FIG. 4 illustrates an exemplary airway status indicator display with three areas of display information. Graphical CO2 waveforms will be shown in area 50. A dynamic progress bar 60 will be shown in area 52. An airway status box 54 is colored to indicate the instantaneous or final determination of the airway analysis. FIG. 4 shows the display upon initialization. No information is displayed and the airway status box 54 is filled with a neutral yellow color.

Figure 5:
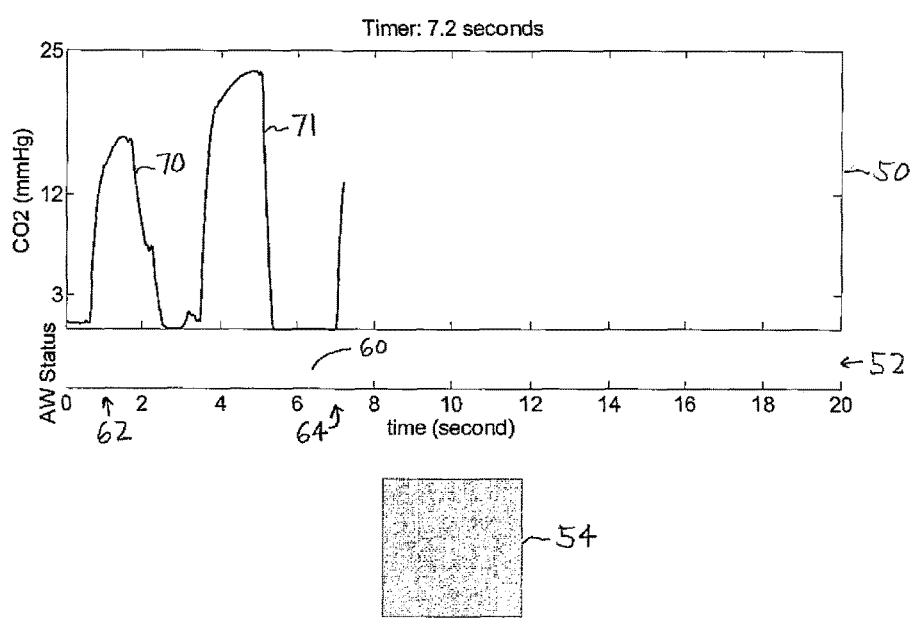
FIG. 5 illustrates the display of FIG. 4 seven seconds after successful airway placement.

FIG. 5 illustrates the display of FIG. 4 after CO2 samples have been received for 7.2 seconds, as indicated by the timer at the top of the graphical display 50. The status color of both the progress bar 60 and the airway status box 54 starts in the yellow color, During the first 5 seconds of respiration data the progress bar remains yellow as indicated at 62. Although two breaths 70 and 71. are seen in the waveform box 50, neither has yet been validated as a true breath by the automated program. Hence, the status box 54 remains yellow and the tint of the progress bar begins to turn orange as it trends toward red in the absence of a valid breath as indicated at 64. The waveform data shown is from an intubated patient who has been resuscitated from cardiac arrest and the CO2 content of the exhalation breaths are in the range of 12-25 mm Hg, indicating very low perfusion and CO2 expression in the body. CO2 monitors such as that of the MRx monitor defibrillator are capable of displaying CO2 output in either % concentration in the exhaled air or in mm Hg, where 5%-6% CO2 concentrations equate to 35-40 mm Hg.

Figure 6:
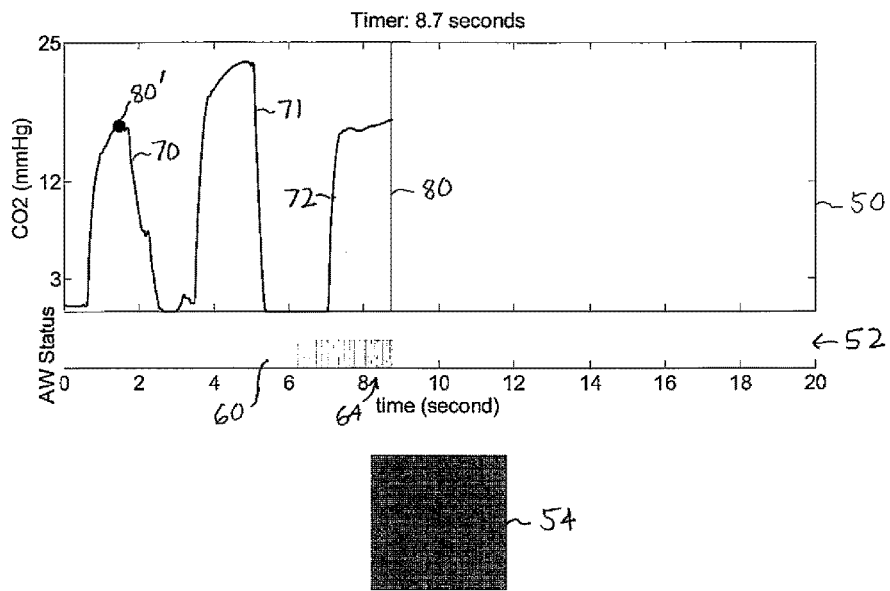
FIG. 6 illustrates the display of FIG. 5 after a first true breath has been validated.

At a time of 8.7 seconds the first breath 70 is validated as a true breath by the automated program as shown in FIG. 6. A breath is validated as a true breath based on known measurable characteristics of the CO2 waveform. For example, the height of the CO2 waveform 70 may be considered. Waveforms above a predetermined amplitude such as 3 mm Hg may be considered valid. Another waveform characteristic which may be considered is the duration of the waveform. A valid breath should exhibit a duration of at least 200 msec, for instance, and not greater than several seconds to be considered valid. Other characteristics of the pulse shape may also be taken into consideration such as the rise, fall, and slope of the waveform. Further details of the processing of a CO2 waveform analysis program may be found in concurrently filed U.S. patent application Ser. No. 14/000,535, entitled "CAPNOGRAPHY SYSTEM FOR AUTOMATIC DIAGNOSIS OF PATIENT CONDITION," of which the present inventors are co-inventors. This application is incorporated herein by reference.

In the example of FIG. 6 a green bar 80 is placed on the CO2 waveform display at an 8.7 time marker on the display to indicate that a true breath has been validated. The waveform 70 which has been validated in this example is also marked with a green dot 80'. Since a true breath has been identified the progress bar 60, which has been trending toward red, now will begin to be colored green starting from the 8.7 time marker, and will remain green for at least two seconds. The status box 54 is also now shown in green.

Figure 7:
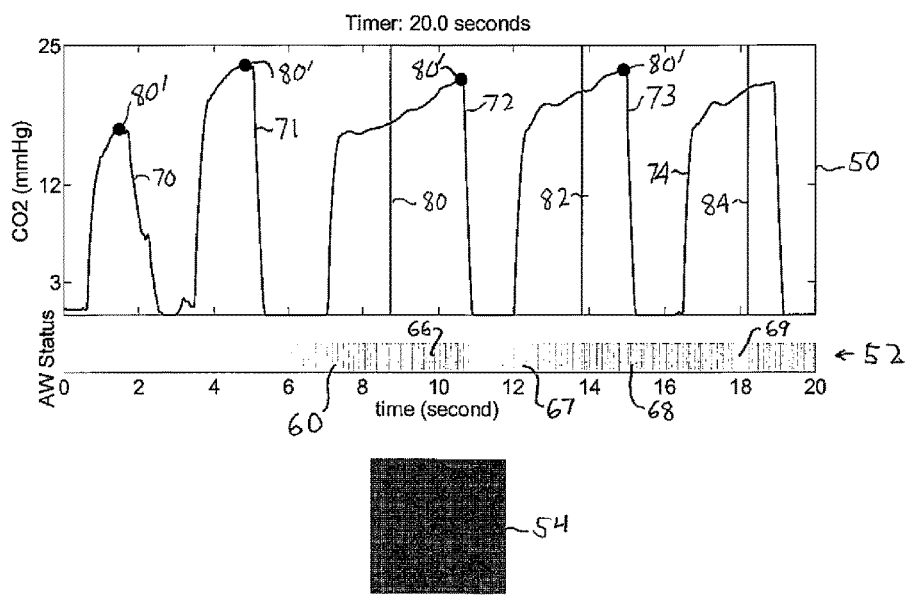
FIG. 7 illustrates the display of FIG. 6 after twenty seconds of breath analysis.
Figure 8:
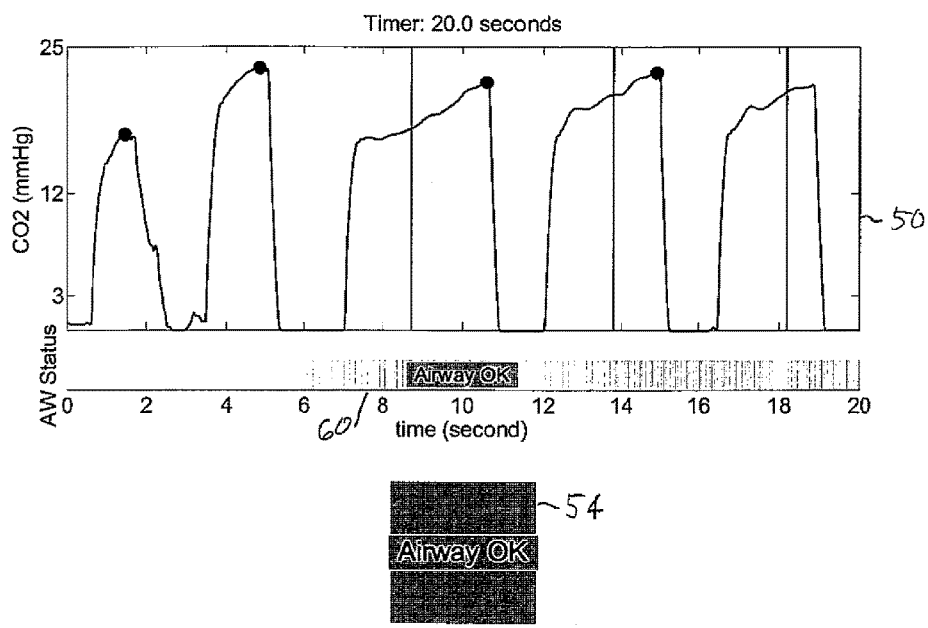
FIG. 8 illustrates the display of FIG. 7 after determination of successful airway placement.

FIG. 7 shows the display after 20 seconds of analysis. In this example the first four breaths 70-73 have been validated as true breaths as indicated by the green dots 80'. The times of validation of the first three of these breaths are marked by the color bars 80, 82 and 84 at the times indicated by the time scale. In this example the progress bar 60 remained green for two seconds after the first breath validation, from 8.7 to 10.7 seconds as indicated by 66. Since another true breath had not been found by the 10.7 second mark, the progress bar turned yellow again at that time and remained yellow as indicated at 67 until a second true breath was validated at time 13.8 seconds, at which time the progress bar turned green again. After validation of a second true breath the progress bar remains green for at least 4 seconds in this example as indicated at 68. At time 17.8 seconds the progress bar turned yellow again but only for a short interval indicated at 69 because a third true breath was validated at time 18.2 seconds, causing the progress bar to turn green again. At the end of the 20 second analysis period the progress bar 60 and the status box 54 are both green in this example.

At the end of the twenty second period the automated program has found enough true breaths and done enough analysis to determine that the placement of the airway device is correct, and causes an Airway OK advisory to be displayed. In this example the Airway OK advisory is displayed over both the progress bar 60 and the green airway status box 54. The physician or medical technician now knows that the intubation has been successfully located in the trachea and not in the esophagus or elsewhere in the throat.

Figure 9:
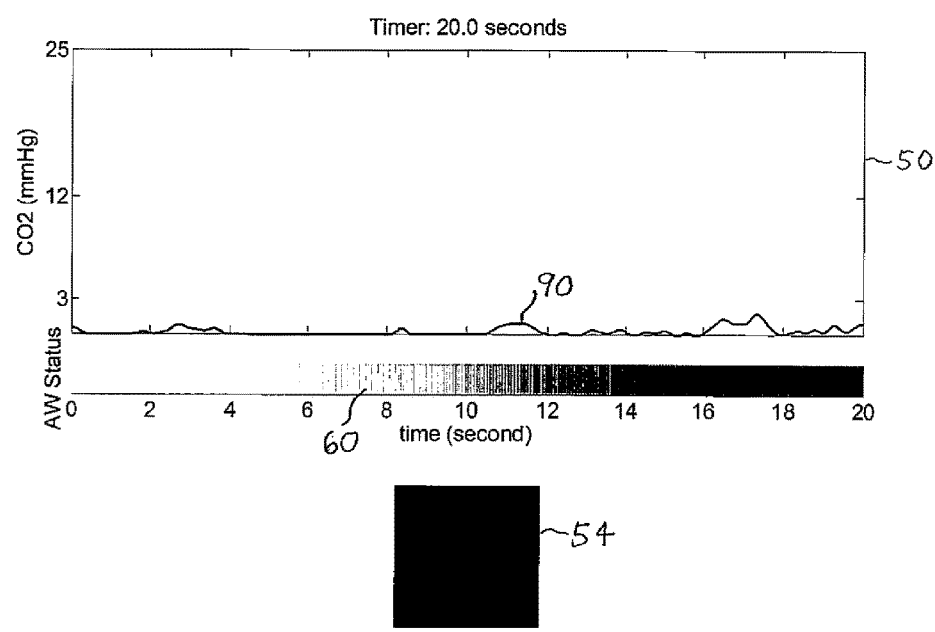
FIG. 9 illustrates a real-time airway status indicator display of the present invention after twenty seconds of analysis of a failed airway placement.
Figure 10:
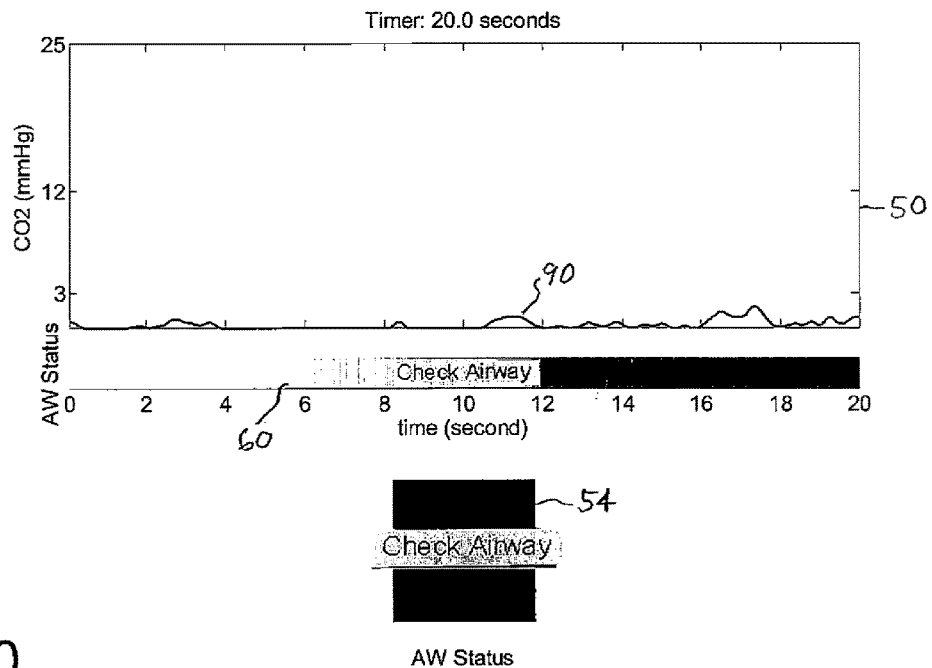
FIG. 10 illustrates the display of FIG. 9 after determination of a failed airway placement.

FIG. 9 is an example of an airway status display of the present invention in which the airway device is improperly located in the esophagus. The CO2 waveform display 90 is seen to show no discernable breath waveforms. The progress bar 60 started with a yellow color and after 5 seconds the tint began to change toward red. The progress bar progressively turned orange in the middle of the time interval and progressed to a distinct red color by the end of the twenty second analysis period. At the illustrated twenty second time mark, the airway status box 54 is also a distinct red color. At this time the automated program has made a determination that the airway placement is incorrect and displays a Check Airway warning. In this example the Check Airway warning is displayed over both the progress bar 60 and the red airway status box 54 as shown in FIG. 10.

Figure 11:
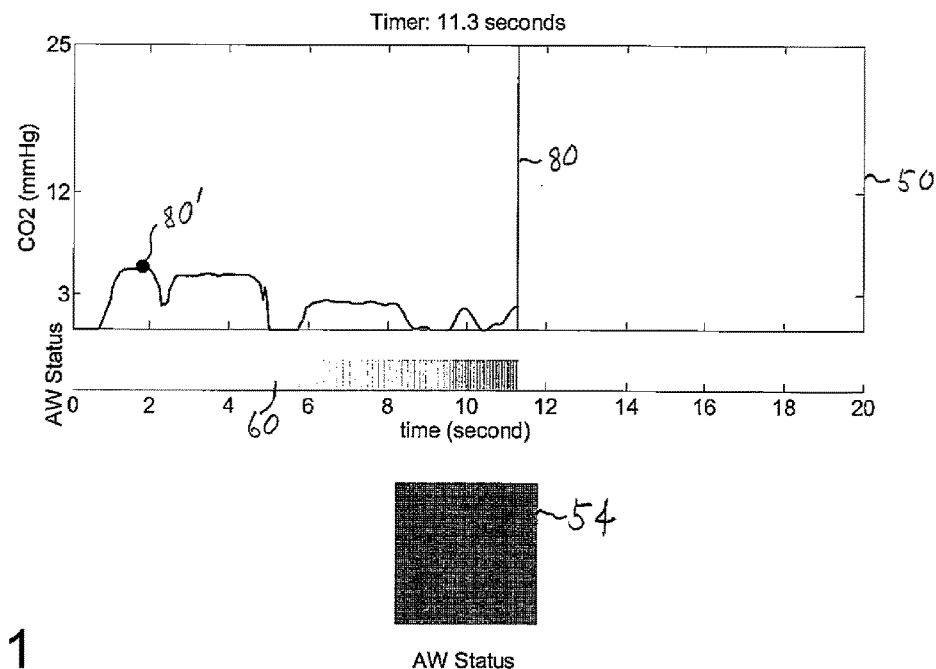
FIG. 11 illustrates a real-time airway status indicator display of the present invention after eleven seconds of analysis with only one breath validated.
Figure 12:
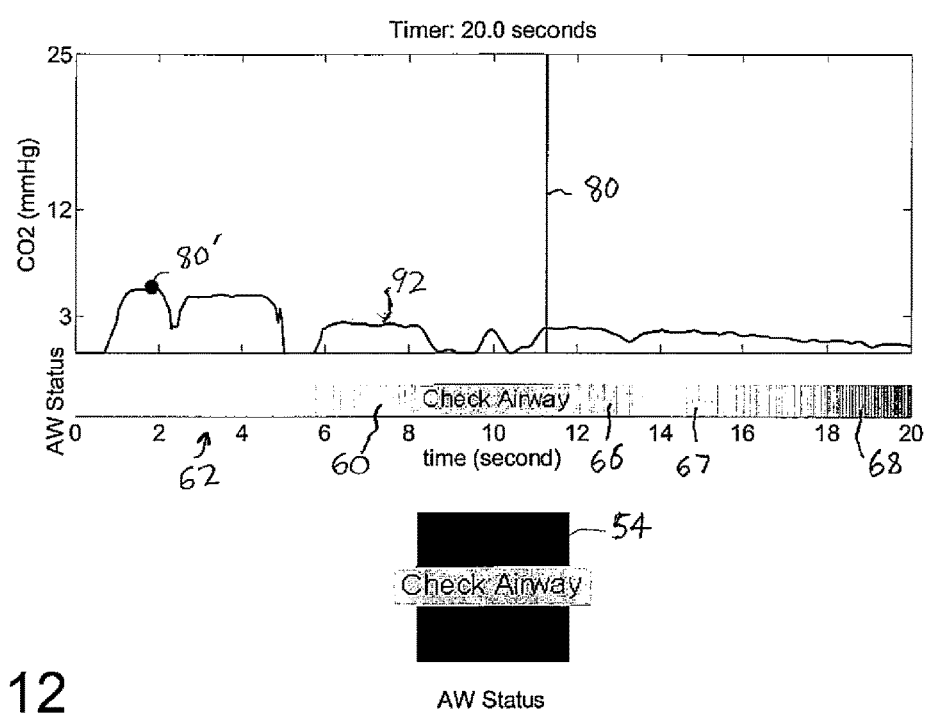
FIG. 12 illustrates the display of FIG. 11 after determination of a failed airway placement.

FIG. 11 illustrates another example of an airway status display of the present invention in which a valid breath, indicated by the green dot 80', was identified at time 11.3 seconds as indicated by green bar 80. This causes the next two seconds, after time 11.3 seconds, of the progress bar 60 to be displayed in a green color. Prior to time 11.3 seconds the progress bar was yellow and trending toward red. With the identification of a valid breath, the progress bar 60 then changes to green for the next two second, as does the airway status box 54. The two second green interval 66 of the progress bar 60 is indicated in FIG. 12. But since no other true breath is identified the progress bar thereafter changes to yellow as indicated at 67 and trends toward red by the end of the twenty second interval as indicated at 68, as does the airway status box 54. The final decision on airway placement by the automated program is failed intubation because no second valid breath was found, and the Check Airway warning is displayed to the user as shown in FIG. 12. The CO2 waveform of this example is that of a patient who has experienced an esophageal intubation and not a successful tracheal intubation.

The above examples show different ways to display the real time progress of airway check and successful or failed placement to a user. In a constructed embodiment different ones of the display formats may be employed, individually or in combination as decided by the system designer. On the MRx defibrillator monitor, for instance, only the CO2 waveforms are shown in the graphical display, without the validation bars 80 or dots 80', as the colors of the progress bar 60 convey essentially the same information. Other implementations may choose to display either the dynamically updated progress bar 60 or the color-variable airway status indicator 54, at the option of the designer.

What is claimed is:

1. A respiration monitoring system which assesses a success or failure of airway device placement comprising:
   a sensor which senses respiration through an airway device and produces respiration signals;
   a processor adapted to analyze the respiration signals and identify a valid breath; and
   a display responsive to the processor which provides real time visual feedback of the success or failure of airway device placement which comprises:
   a continuously updated dynamic indicator of the progress of analysis of airway device placement, responsive to and updated by each identification of a valid breath by the processor, which presents a real time color-coded indication of the progress toward successful airway device placement; and wherein the continuously updated dynamic indicator further comprises a progress bar which becomes a characteristic color:
for a first time interval following identification of a first valid breath; and
for a second time interval following identification of a second valid breath, wherein the second time interval is longer than the first time interval.

2. The respiration monitoring system of claim 1, wherein the display further comprises a continuously updated graphical display of respiration breaths.

3. The respiration monitoring system of claim 2, wherein the graphical display further comprises a $CO_2$ breath waveform with time-delineated indicators of the validation of a true breath, and wherein the time-delineated indicators of identifications of valid breaths are displayed on the graphical display.

4. The respiration monitoring system of claim 3, wherein a graphical waveform which has been identified as a valid breath is visually distinguished on the display.

5. The respiration monitoring system of claim 1, wherein the progress bar is incremented in correspondence with the production or processing of respiration signals.

6. The respiration monitoring system of claim 5, wherein the progress bar is colored in correspondence with identifications of valid breaths.

7. The respiration monitoring system of claim 6, wherein the progress bar is colored green in correspondence with the identification of the first valid breath, and is colored with a yellow-red tint in correspondence with the absence of the identification of the second valid breath.

8. The respiration monitoring system of claim 7, wherein, in the absence of the identification of the second valid breath, the progress bar progressively changes from yellow to red over time.

9. The respiration monitoring system of claim 1, wherein the display further comprises a variably colored indicator of an instantaneous and final determination of the success or failure of airway device placement,
wherein the variably colored indicator is colored green in correspondence with the identification of the first valid breath, red in correspondence with the determination of failed airway device placement, and yellow in indeterminate periods.

10. The respiration monitoring system of claim 9, wherein the variably colored indicator is colored green upon a final determination of successful airway device placement, and red upon a final determination of faded airway device placement.

11. The respiration monitoring system of claim 1, wherein the processor is further adapted to cause the display to display a message of successful or failed airway device placement.

12. The respiration monitoring system of claim 11, wherein the processor is further adapted to analyze the respiration signals to make a final determination of successful or failed airway device placement,
wherein the message is displayed upon the making of a final determination.

13. The respiration monitoring system of claim 1, wherein the display further comprises a $CO_2$ breath waveform, and wherein a breath waveform segment is identified as a valid breath based upon the amplitude, duration, and shape of the breath waveform segment.

14. The respiration monitoring system of claim 1, wherein an identification of a valid breath is based on a $CO_2$ breath waveform amplitude.

15. The respiration monitoring system of claim 1, wherein an identification of a valid breath is based on corners and slopes of a $CO_2$ breath waveform.

16. The respiration monitoring system of claim 1, wherein:
the characteristic color is green; and
the progress bar becomes red if a predetermined time period expires before the time of identification of the first valid breath.

17. The respiration monitoring system of claim 1, wherein the characteristic color is green.

18. The respiration monitoring system of claim 1, wherein the continuously updated dynamic indicator becomes the characteristic color for a third time interval following identification of a third valid breath, wherein the third time interval is longer than the second time interval.

19. A respiration monitoring system for assessing a success or failure of an airway device placement comprising:
a display device;
one or more processors configured to:
receive respiration signals from a sensor of the airway device;
analyze the respiration signals and identify a valid breath; and
provide real time visual feedback of the success or failure of airway device placement on the display device;
provide, on the display device, a continuously updated dynamic indicator of the progress of analysis of airway device placement,
update, with each identification of a valid breath, the continuously updated dynamic indicator of the progress of analysis of airway device placement to present a real time color-coded indication of the progress toward successful airway device placement; and
wherein the continuously updated dynamic indicator further comprises a progress bar which becomes a green color:
for a first time interval following a first identification of a first valid breath; and
for a second time interval following a second identification of a second valid breath, wherein the second time interval is longer than the first time interval.

20. The respiration monitoring system of claim 19, wherein:
the continuously updated dynamic indicator becomes green for a third time interval following a third identification of a third valid breath, wherein the third time interval is longer than the second time interval; and
in the absence of an identification of a valid breath, the progress bar is colored with a yellow-red tint.

* * * * *